United States Patent [19]

Waller et al.

[11] Patent Number: 5,502,243

[45] Date of Patent: Mar. 26, 1996

[54] HYDROCARBONYLATION OF DIMETHYL ETHER

[75] Inventors: Francis J. Waller, Allentown; David W. Studer, Wescosville, both of Pa.

[73] Assignee: Air Products and Chemicals, Inc., Allentown, Pa.

[21] Appl. No.: 308,018

[22] Filed: Sep. 16, 1994

Related U.S. Application Data

[63] Continuation-in-part of Ser. No. 963,771, Oct. 20, 1992, abandoned, which is a continuation-in-part of Ser. No. 870,126, Apr. 15, 1992.

[51] Int. Cl.⁶ .................................................. C07C 67/36
[52] U.S. Cl. .................................................. 560/232
[58] Field of Search .................................................. 560/232

[56] References Cited

U.S. PATENT DOCUMENTS

| | | | |
|---|---|---|---|
| 4,319,038 | 3/1982 | Kübbeler et al. | 560/232 |
| 4,323,697 | 4/1982 | Riskalla | 560/232 |
| 4,429,150 | 1/1984 | Drent | 560/232 |
| 4,430,096 | 2/1984 | Schnur et al. | 48/206 |
| 4,659,864 | 4/1987 | Isshiki | 560/240 |
| 4,810,821 | 3/1989 | Paulik et al. | 560/232 |
| 4,843,170 | 6/1989 | Isshiki et al. | 560/261 |
| 5,003,104 | 3/1991 | Paulik | 560/232 |
| 5,117,046 | 5/1992 | Paulik et al. | 560/232 |
| 5,138,093 | 8/1992 | Rizkalla | 560/232 |
| 5,218,003 | 6/1983 | Lewnard et al. | 518/700 |

FOREIGN PATENT DOCUMENTS

| | | |
|---|---|---|
| 35860 | 9/1981 | European Pat. Off. . |
| 58442 | 8/1982 | European Pat. Off. . |
| 77116 | 4/1983 | European Pat. Off. . |
| 324475 | 7/1989 | European Pat. Off. . |
| 2610035 | 9/1976 | Germany . |
| 1538782 | 1/1979 | United Kingdom . |

OTHER PUBLICATIONS

Sheldon, "Chemicals From Synthesis Gas," pp. 1–20, 140–149 & 164–166 (1983).

Lewnard, J. J. et al. "Single–Step Synthesis of Dimethyl Ether in a Slurry Reactor." *Chemical Engineering Science* vol. 45 No. 8 1990: 2735–2741.

*Primary Examiner*—Michael L. Shippen
*Attorney, Agent, or Firm*—John M. Fernbacher

[57] ABSTRACT

Oxygenated acetyl compounds ethylidene diacetate, acetic acid, acetic anhydride, acetaldehyde, and methyl acetate are produced directly from synthesis gas and dimethyl ether in a catalyzed liquid phase reaction system. The inclusion of carbon dioxide in the synthesis gas in selected amounts increases the overall yield of oxygenated acetyl compounds from the reactant dimethyl ether. When methanol is included in the reactor feed, the addition of carbon dioxide significantly improves the molar selectivity to ethylidene diacetate.

19 Claims, 3 Drawing Sheets

HYDROCARBONYLATION OF DIMETHYL ETHER

This application is a continuation-in-part of U.S. Ser. No. 07/963,771 filed Oct. 20, 1992, now abandoned, which is a continuation-in-part of U.S. Ser. No. 07/870,126 filed Apr. 15, 1992, the specifications of which are incorporated herein by reference.

FIELD OF THE INVENTION

This invention relates to an integrated process for synthesizing ethylidene diacetate, acetic anhydride, acetaldehyde, methyl acetate, and acetic acid, and in particular the production of these oxygenated acetyl compounds from synthesis gas via the intermediate compound dimethyl ether.

BACKGROUND OF THE INVENTION

Ethylidene diacetate (EDDA) is a valuable intermediate in the production of vinyl acetate (VAc), and considerable interest has been focused on developing improved processes for producing ethylidene diacetate. The commercial success of these improved processes, however, requires a market for the acetic acid (HOAc) which is a coproduct of vinyl acetate production. The acetic acid can be sold, esterified with methanol to methyl acetate (MeOAc or MA), or alkylated with dimethyl ether (DME) to methyl acetate and methanol (MeOH). Methyl acetate (MeOAc), acetaldehyde (AcH), and acetic anhydride ($Ac_2O$) are also important as intermediates for the production of other valuable products.

Representative processes for preparing EDDA include German Specification 2,610,035 which discloses a process for producing EDDA wherein the acetic acid obtained as a coproduct can be directly obtained by distillation processes and purified so that it can be used as such or reacted with methanol to form methyl acetate.

British Specification No. 1,538,782 describes a process for producing EDDA wherein dimethyl ether (DME) and/or methyl acetate, carbon monoxide and hydrogen are reacted in the presence of a catalyst system. The reaction preferably occurs in the presence of a Group VIII metal catalyst and a promoter such as an organo-phosphine and/or organo-nitrogen compound.

European Specification No. 35,860 discloses a process for producing EDDA and/or acetaldehyde wherein dimethyl ether or methyl acetate, carbon monoxide and hydrogen are reacted in the presence of a supported palladium catalyst and an halide.

An improved process is described in U.S. Pat. No. 4,319,038 for preparing EDDA and acetic anhydride wherein methyl acetate and/or dimethyl ether, carbon monoxide and hydrogen are reacted in the presence of a quaternary nitrogen, and a manganese or rhenium compound.

European Specification No. 77116 discloses a process for producing EDDA wherein dimethyl ether and/or methyl acetate, carbon monoxide and hydrogen are reacted in the presence of a catalyst system comprising a rhodium compound, a halogen component and a palladium co-catalyst.

European Specification No. 58,442 discloses a process for the coproduction of an alkylidene dicarboxylate and a carboxylic acid by the hydrogenation of a carboxylic acid anhydride in the presence of carbon monoxide and a homogeneous Group VIII metal catalyst together with a chloride, bromide, or iodide and a promoter comprising an organo oxygen, nitrogen, phosphorous, arsenic, or antimony compound having a lone pair of electrons.

U.S. Pat. No. 4,323,697 discloses a process for preparing EDDA wherein methyl acetate and/or dimethyl ether, carbon monoxide and hydrogen are reacted in the presence of a molybdenum-nickel or tungsten-nickel co-catalyst in the presence of a promoter comprising an organo-phosphorous compound or an organo-nitrogen compound. When dimethyl ether is utilized, the reference teaches that a reactor having two reaction zones is preferred. In the first zone, DME is converted by carbonylation to methyl acetate and the second zone is devoted to conducting the EDDA-forming reaction.

U.S. Pat. No. 4,429,150 which discloses a process for producing EDDA wherein methyl acetate and/or dimethyl ether, carbon monoxide and hydrogen are reacted in the presence of a catalyst system comprising a Group VIII metal and a halogen-containing compound in the presence of a sulphur-containing polar solvent, e.g. sulpholane. The reference teaches that organo-phosphorous compounds improve selectivity and increase conversion to EDDA.

An integrated process for the production of synthesis gas is described in U.S. Pat. No. 4,430,096 wherein one or more organic compounds are converted into hydrogen and carbon monoxide by partial oxidation in the presence of steam and/or carbon dioxide. The heat for the reaction is provided by direct heat exchange with products from the gasification of coal with oxygen and steam.

U.S. Pat. No. 4,843,170 discloses a process for preparing vinyl acetate wherein dimethylacetal and acetic anhydride are converted to EDDA and methyl acetate in one of the steps.

U.S. Pat. Nos. 4,810,821 and 5,117,046 disclose the synthesis of ethylidene diacetate by reacting hydrogen and an ether such as dimethyl ether in a catalyzed reactor system. Several different catalyst systems are used to promote the reactions. It is specifically taught that $CO_2$, if present in the reaction system, is an inert diluent or impurity which does not react with other components in the system.

The preparation of dimethyl ether from synthesis gas in a single stage liquid phase reactor containing solid methanol synthesis and methanol dehydration catalysts slurried in an inert oil is disclosed in European Patent Application 0 324 475 A1, in the article entitled "Single-step Synthesis of Dimethyl Ether in a Slurry Reactor" by J. J. Lewnard et al in *Chemical Engineering Science* Vol. 45, No. 8, pp. 2735–2741, 1990, and in U.S. Pat. No. 5,218,003.

EDDA thus can be produced by several different process sequences according to the prior art. There is need for an improved integrated process for producing EDDA from synthesis gas with controlled coproduction of acetic acid, and in specific cases with minimum coproduction of acetic acid, while simultaneously maximizing carbon utilization in the synthesis gas feed. In addition, there is need for an improved method for producing vinyl acetate from EDDA with minimum coproduction of acetic acid. Further, the coproduction of the valuable compounds methyl acetate and acetic anhydride is desirable under certain market conditions. The invention described in the following specification and defined by the appended claims provides a new integrated process which fulfills these needs.

SUMMARY OF THE INVENTION

The present invention is a process for the synthesis of ethylidene diacetate which comprises reacting a feed containing dimethyl ether, methanol, and synthesis gas which contains hydrogen, carbon monoxide, and carbon dioxide in a liquid phase reactor containing at least acetic acid and a catalyst system consisting essentially of a Group VIII metal, methyl iodide, lithium iodide, and lithium acetate at conditions sufficient to produce ethylidene diacetate and one or more additional oxygenated acetyl compounds, wherein the molar ratio of carbon dioxide to methanol in the feed is between 5 and 12. Preferably the molar ratio of dimethyl ether to methanol in the feed is between 3 and 11. The one or more additional oxygenated acetyl compounds can include acetaldehyde, acetic acid, acetic anhydride, and methyl acetate.

The invention also includes a process for the synthesis of ethylidene diacetate which comprises reacting synthesis gas comprising hydrogen, carbon monoxide, and carbon dioxide in a first liquid phase reactor in the presence of a methanol synthesis catalyst and a methanol dehydration catalyst suspended in an inert liquid at conditions sufficient to react the components in said feed with acetic acid to produce dimethyl ether and methanol. An intermediate stream comprising dimethyl ether, methanol, and unreacted synthesis gas which contains hydrogen, carbon monoxide, and carbon dioxide is withdrawn from the first reactor and introduced into a second liquid phase reactor containing at least acetic acid and reacting the dimethyl ether, methanol, and unreacted synthesis gas with acetic acid in the presence of a catalyst system consisting essentially of a Group VIII metal, methyl iodide, lithium iodide, and lithium acetate at conditions sufficient to produce said ethylidene diacetate and one or more additional oxygenated acetyl compounds. The critical element of the invention is that the molar ratio of carbon dioxide to methanol in the intermediate stream is between 5 and 12. Preferably the molar ratio of dimethyl ether to methanol in the intermediate stream is between 3 and 11. The one or more additional oxygenated acetyl compounds can include acetaldehyde, acetic acid, acetic anhydride, and methyl acetate. The methanol synthesis catalyst comprises copper and the methanol dehydration catalyst comprises alumina, wherein the methanol synthesis catalyst is between 75 and 90% of the methanol synthesis catalyst plus methanol dehydration catalyst on a weight basis.

In a process for synthesizing one or more oxygenated acetyl compounds selected from the group consisting of ethylidene diacetate, acetaldehyde, acetic acid, acetic anhydride, and methyl acetate from a feed containing dimethyl ether, hydrogen, and carbon monoxide in a liquid phase reactor in the presence of a catalyst system consisting essentially of a Group VIII metal, methyl iodide, and lithium iodide, the present invention is the improvement which comprises increasing the yield of oxygenated acetyl compounds by adding carbon dioxide to the feed such that the molar ratio of carbon dioxide to dimethyl ether is between 0.3 and 1.3, wherein said liquid phase reactor contains at least acetic acid.

The present invention has several advantages over prior art methods for producing EDDA and other oxygenated acetyl compounds. First, the molar selectivity to ethylidene diacetate is improved by the addition of carbon dioxide when methanol is included in the reactor feed. Second, the feed to the oxygenated acetyl reactor can be operated from a liquid phase dimethyl ether reactor system which provides the requisite feed containing dimethyl ether, methanol, hydrogen, carbon dioxide, and carbon dioxide.

The invention also improves the overall yield of acetyl compounds under certain conditions by the addition of carbon dioxide to the reactor feed.

DETAILED DESCRIPTION OF THE INVENTION

Figure 1:
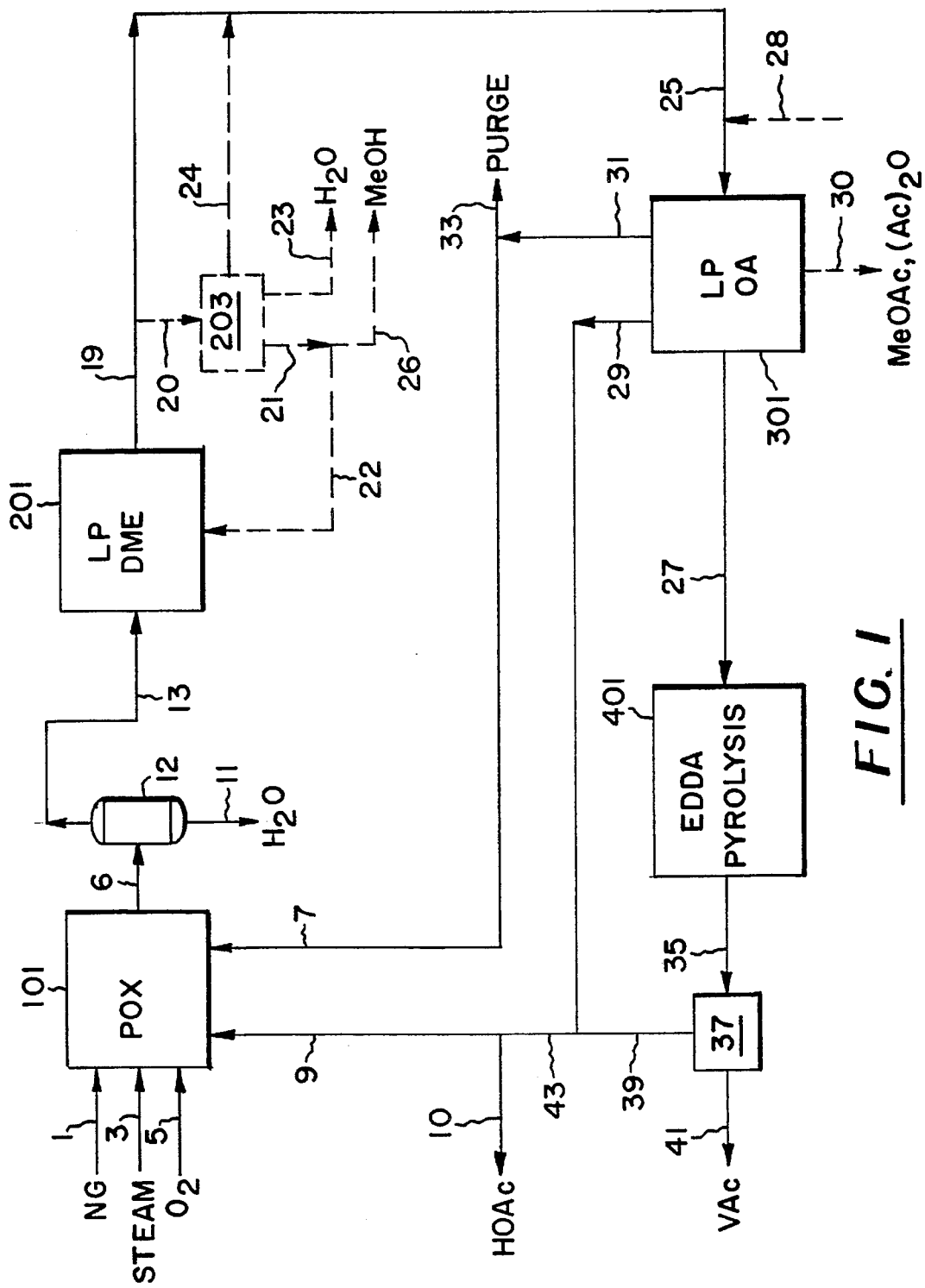
FIG. 1 is a block diagram of the integrated process of the present invention.

A process block flow diagram for the overall integrated process is shown in FIG. 1. Hydrocarbon feedstock 1, preferably natural gas, is fed with steam 3 and oxygen 5 into partial oxidation (POX) reactor 101 to produce raw synthesis gas 6 containing typically 25 to 65 vol % hydrogen, 30 to 50 vol % carbon monoxide, 0.5 to 12 vol % carbon dioxide, 0 to 0.5 vol % methane, and 2 to 25 vol % water. The hydrocarbon feedstock alternately can be selected from methane, $C_2^+$ gaseous hydrocarbons, naphtha, gas oil, vacuum residuum, and various other combustible hydrocarbons including petroleum coke and coal. POX processes for synthesis gas generation are well known in the art and are offered commercially by Texaco and Shell, among others. Steam is both a reactant and a temperature moderant in the POX reactor. $CO_2$-rich unreacted synthesis gas recycle stream 7 typically containing 60–70 vol % $CO_2$ is introduced optionally into the POX reactor, wherein the $CO_2$ is both a reactant and a temperature moderant. In some cases, depending on the hydrocarbon feedstock used, the $CO_2$-rich recycle stream 7 may eliminate the need for steam 3. Coproduct acetic acid recycle stream 9 provides additional hydrocarbon feed to the POX unit and is converted into additional syngas, thus reducing the hydrocarbon feedstock requirement. A portion 10 of acetic acid stream 9 optionally is withdrawn as an external product.

Condensable water 11 is removed in separator 12 and dry syngas 13 passes into liquid phase dimethyl ether (DME) reactor system 201. Optionally, depending on the overall process carbon balance requirements, a portion of the hydrogen in feed 13 can be removed by pressure swing adsorption or cryogenic distillation. Product stream 19, comprising DME, methanol, unreacted synthesis gas (including $CO_2$), and water, preferably passes directly to LP OA reactor system 301 as stream 25. Alternatively, stream 19 passes as stream 20 to separation system 203 which yields methanol stream 21, water 23, and intermediate product stream 25 comprising DME and unreacted synthesis gas. Optionally, a portion 26 of methanol stream 21 is taken as an external product and another portion 22 is recycled to the LP DME reactor system. Alternatively, at least a portion of the carbon dioxide in stream 25 is removed by methods known in the art prior to the LP OA reactor system described below. Optionally, carbon dioxide 28 can be imported and added to stream 25 to increase the carbon dioxide content. As illustrated in the Examples which follow, the preferred range of the DME/MeOH molar ratio for improved EDDA selectivity is about 3 to 11, although higher ratios are expected to give still higher EDDA selectivity. The preferred range of the molar ratio $CO_2$/MeOH is about 3 to 15, and more preferably 5 to 12. These preferred ranges can be realized when the feed to LP oxygenated acetyl reactor system 301 of FIG. 1 is provided directly from liquid phase dimethyl ether reactor system 201. This preferred mode of operation requires no additional treatment of effluent stream 19 of reactor system 201 as long as the water content is below about 2 mol %. Water optionally can be removed by condensation if present at higher concentrations. Feed composition, catalyst composition, and operating conditions in DME reactor system 103 can be controlled to yield the preferred composition range in feed 25 to reactor system 301. Optionally $CO_2$ 28 can be added if required.

Alternatively, some or all of the hydrogen in the unreacted synthesis gas from the LP DME reactor can be removed by condensing the DME and methanol and separating the resulting synthesis gas by known methods of pressure swing adsorption (preferably) or cryogenic distillation.

Oxygenated acetyl (OA) reactor system 301 comprises a liquid phase reactor in which DME, methanol, acetic acid, and synthesis gas react in the presence of one or more catalysts described below to yield EDDA and intermediates or coproducts including acetic acid, acetic anhydride, methyl acetate, and acetaldehyde. EDDA product 27, acetic acid 29, and unreacted synthesis gas 31 are separated from other coproducts which are recycled within reactor system 301. Optionally, a portion 30 of the coproducts acetic anhydride and methyl acetate can be withdrawn and separated into individual products. A small portion 33 of unreacted synthesis gas 31 is removed as purge, and the remainder 7 is recycled to POX reactor 101. EDDA product passes into EDDA pyrolysis system 401 where EDDA is thermally cracked to yield intermediate product 35 containing acetic acid (HOAc) and vinyl acetate (VAc), and this stream passes to separation system 37 which yields acetic acid 39 and vinyl acetate product 41. EDDA pyrolysis in system 401 and product separation in system 37 are known in the art, and any commercially available process is suitable for this purpose. A description of a commercial EDDA pyrolysis reaction and separation system is given for example in SRI Report No. 146, Process Economics Program Series, Stanford Research Institute, 1981.

Acetic acid streams 29 and 39 are combined into a total coproduct acetic acid stream 43, a portion 10 optionally is taken as a product, and the remainder 9 is recycled to POX reactor system 101 to generate additional synthesis gas. The amount of acetic acid product 10 will depend upon market and pricing conditions at a given plant location, and if desired the entire acetic acid stream 43 can be recycled to POX reactor system 101. Typically about 0 to 50% of stream 43 is taken as acetic acid product 10.

Figure 2:
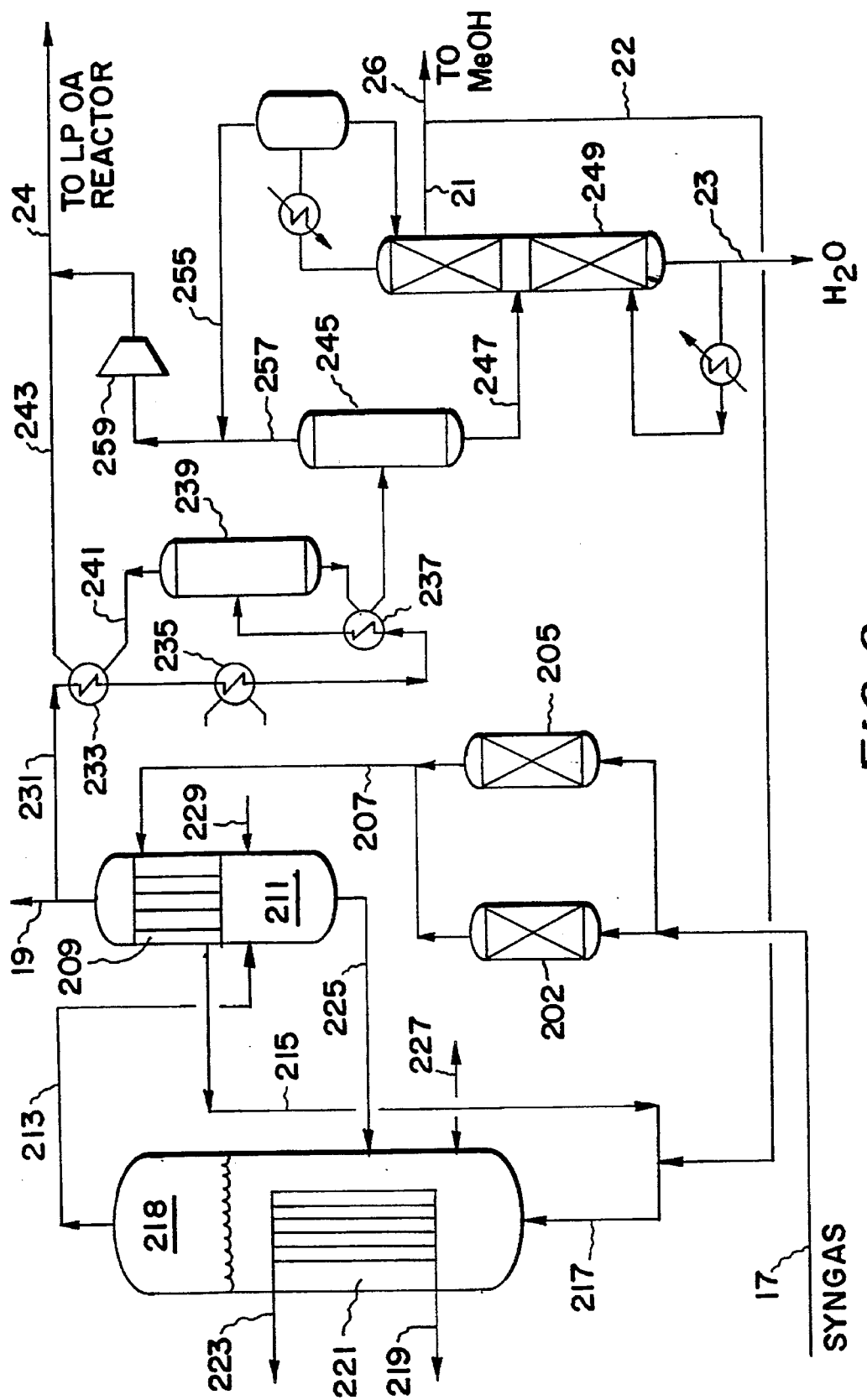
FIG. 2 is a general flow diagram of the liquid phase dimethyl ether reactor and separation system of the present invention.

DME reactor system 201 is illustrated in more detail in FIG. 2 and in U.S. Pat. No. 5,218,003, the specification of which is incorporated herein by reference. Feedstream 17 (equivalent to stream 13 of FIG. 1) is treated in alternating adsorbers 203 and 205 to remove metal carbonyl compounds and other contaminants which are detrimental to the DME synthesis catalysts. Clean syngas 207 is heated to 300° to 430° F. in exchanger 209 in vessel 211 by indirect heat exchange with DME reactor effluent 213, heated syngas 215 is optionally combined with methanol recycle 22, and combined feed 217 is introduced into liquid phase DME reactor 218. DME reactor 218 contains a methanol synthesis catalyst and a methanol dehydration catalyst, both in powdered form with an average particle size between about 5 and 50 microns, suspended in an inert liquid. The methanol synthesis catalyst is selected from commercially-available copper/zinc-based catalysts, preferably a $Cu/ZnO/Al_2O_3$ catalyst such as the widely-used BASF S3-86. The methanol dehydration catalyst is selected from alumina, silica-alumina, zeolites such as ZSM-5, solid acids such as boric acid, solid acidic ion-exchange resins, and mixtures thereof. Typically a commercially-available alumina such as Catapal B gamma alumina may be used. The preferred alumina is prepared by heating boehmite (alumina monohydrate, $Al_2O_3 \cdot H_2O$) powder at a rate sufficient to increase the temperature of the alumina by about 100° C. per hour to about 500° C., holding at this temperature for about 3 hours, and cooling the resulting heat-treated alumina to ambient temperature. The inert liquid for the catalyst slurry preferably comprises paraffinic or naphthenic hydrocarbons boiling in the range of 150° to 450° C. Alternatively alcohols, ethers, or polyethers with boiling points in this range can be utilized.

The synthesis gas reacts in the presence of the catalyst suspended in the inert liquid to form methanol and a significant portion of the methanol is dehydrated to form DME. Reactor effluent 213 contains typically 3–13 vol % DME, 1–5 vol % methanol, 40–75 vol % unreacted synthesis gas, and 0.2–1 vol % water. The synthesis and dehydration reactions are exothermic and the heat generated is removed by passing coolant 219 (preferably water) through exchanger 221 and withdrawing heated coolant 223 (preferably steam) therefrom. Reactor effluent 213 is cooled in exchanger 209 against feed 207 to condense and coalesce vaporized and entrained inert liquid, which accumulates in the lower section of vessel 211; the collected liquid 225 is returned to reactor 218. Spent catalyst slurry is withdrawn and fresh catalyst slurry is added to reactor 218 through line 227. Makeup inert liquid 229 is added to vessel 211 as needed. Reactor 218 is operated in the temperature and pressure ranges of 440° to 520° F. and 750–2000 psig respectively. The reactor gas hourly space velocity (GHSV) is typically in the range of 3,000 to 15,000 std. liters/(kg cat·hr). Reactor system product stream 19 preferably passes directly to LP OA reactor system 301 as earlier described with reference to FIG. 1.

In the alternative mode of the invention earlier described, DME-containing stream 231 (equivalent to stream 20 of FIG. 1), which also contains methanol, unreacted synthesis gas, and water, is cooled in exchangers 233, 235, and 237 and passes to separator 239. Vapor 241 comprising unreacted synthesis gas and DME is warmed in exchanger 233 to yield stream 243. Liquid from separator 239 is partially vaporized in exchanger 237 and passes into separator 245, from which methanol-rich liquid stream 247 flows to distillation column 249. This column separates stream 247 into water waste bottoms stream 23, sidestream 21 containing 95–100 vol % methanol, and overhead stream 255 containing DME and unreacted synthesis gas. Stream 255 is combined with stream 257 which also contains DME and unreacted synthesis gas, the combined stream is compressed in compressor 259, and is combined with stream 243 to yield DME-synthesis gas stream 25 which provides the feed to OA reactor system 301 of FIG. 1. A portion 22 of methanol sidestream 21 is recycled to DME reactor 218, and the remainder 26 optionally is taken as a methanol product. Optionally, depending on the desired product slate of the overall process, all of methanol sidestream 21 can be taken as product or can be recycled totally to reactor 218 thereby increasing DME yield in stream 24.

Preferably, as earlier described, stream 19 containing DME, methanol, water, and unreacted synthesis gas is fed as stream 25 directly to OA reactor system 301 of FIG. 1. This preferred mode is possible when stream 231 contains less than about 2 vol % water, preferably less than 1 vol % water.

Figure 3:
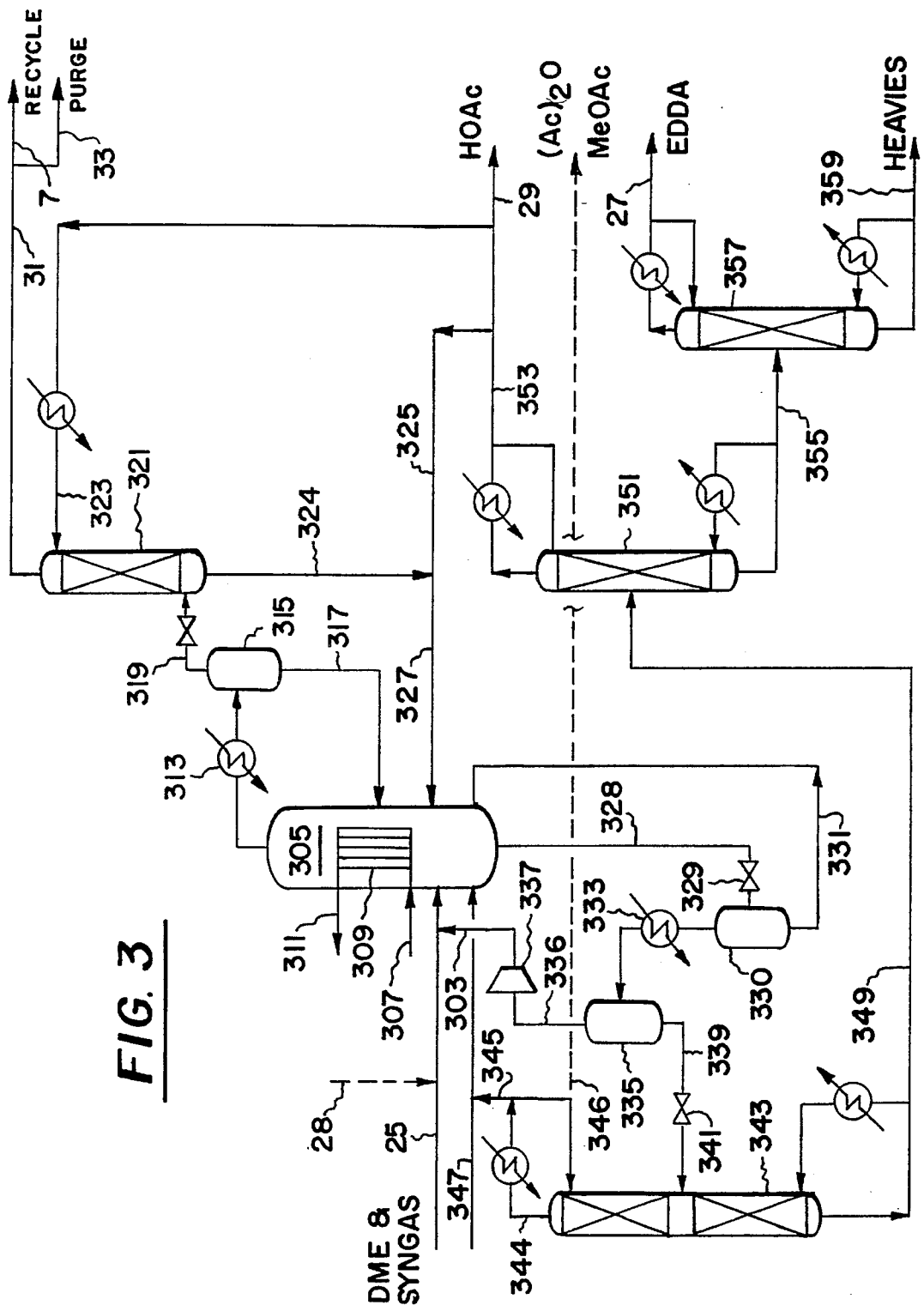
FIG. 3 is a general flow diagram of the liquid phase OA reactor and separation system of the present invention.

The OA reactor system is illustrated in more detail in FIG. 3. Stream 25 from the DME reactor system of FIG. 1 is combined with recycle stream 303 and flows into OA liquid phase reactor 305. Optionally, as earlier described, additional carbon dioxide 28 can be added to stream 25 prior to reactor 305. The liquid phase in the reactor comprises acetic acid, EDDA, and other reaction intermediates or coproducts comprising one or more of the components acetic anhydride, methyl acetate, and acetaldehyde. The major component is acetic acid which comprises about 30 to 80 mol % of the total liquid in the reactor. The liquid contains a catalyst system, preferably soluble therein, which promotes the reaction of dimethyl ether, acetic acid, hydrogen, and carbon monoxide to form EDDA, acetic acid, and the other intermediates or coproducts identified earlier. Thus acetic acid is both a reactant and a product, and comprises the major liquid component in the liquid phase reactor. CO and hydrogen also react with one or more of the intermediates or coproducts identified above in a hydrocarbonylation reaction sequences which yield EDDA and acetic acid. While the exact reaction sequence is not fully understood, it is known in the present invention as later described that EDDA is a product and that acetic acid is a reactant as well as a coproduct. The presence of $CO_2$ in the feed gas can increase acetyl yield, and when methanol is also present in the feed, the presence of $CO_2$ in the feed increases the selectivity to EDDA. This is illustrated in the Examples which follow.

The catalyst system is a new combination of catalysts which provides superior selectivity to EDDA and which can be operated under shorter reaction times than typically required in prior art processes for producing EDDA. The newly discovered catalyst system consists essentially of a Group VIII metal, methyl iodide, lithium iodide, and optionally lithium acetate, which in combination, provide superior results than achieved in prior art processes for producing EDDA which utilize a catalyst system containing less than the combination of these components.

The term hydrocarbonylation as used herein refers to the reaction of dimethyl ether, acetic acid, other intermediate components, hydrogen, carbon monoxide, and carbon dioxide to form one or more of the products EDDA, acetic acid, acetic anhydride, acetaldehyde, and methyl acetate under the described process conditions. Under certain conditions, especially at longer reactor residence times, acetaldehyde will be produced in moderate amounts. Hydrocarbonylation can be carried out in a batch mode or a continuous mode over a wide range of temperatures. While the optimum temperature for practicing the present invention will depend upon process stoichiometry, the particular catalyst system utilized, as well as the precise combination of reaction conditions, suitable hydrocarbonylation temperatures will range from about 20° C. up to about 220° C. However, the most preferred hydrocarbonylation temperatures range from about 120° C. to about 195° C. The hydrocarbonylation reaction can be carried out under a wide variety of pressures including pressures ranging from about 100 psig to about 3000 psig. Preferred pressures range from about 400 psig to about 2100 psig.

The catalyst system of the present invention utilizes a Group VIII metal selected from the group consisting of rhodium, platinum, palladium, iridium, ruthenium, cobalt and nickel with preferred Group VIII metals being rhodium and iridium. The Group VIII metal catalyst used in the catalyst system is present in a catalytically active amount and such catalytically effective amounts can be readily determined by those of ordinary skill in the art. The amount of Group VIII metal to be incorporated into the catalyst system typically ranges from about 0.01 mol % to about 10 mol % based on the DME present, preferably from 0.05 to about 5 mol %. The most preferred Group VIII metal is rhodium.

Examples of suitable rhodium compounds to be incorporated into the catalyst system include rhodium oxide, rhodium (III) hydroxide, rhodium (III) chloride, rhodium (III) chloride trihydrate, rhodium (III) bromide, rhodium (III) iodide, rhodium (II) acetate, tetrarhodium dodecaacetyl, hexarhodium hexadecaacetyl, rhodium (I) diacetyl acetylacetonate, tris(pyridine)rhodium (III) chloride, chlorotris-(triphenylphosphine) rhodium and other organo-rhodium complexes. The preferred rhodium compound to be incorporated into the catalyst system is rhodium (III) chloride trihydrate which is commercially available in hydrated forms.

Examples of suitable palladium compounds to be incorporated into the catalyst system include palladium chloride, palladium chloride dihydrate, palladium bromide, palladium iodide, palladium oxide, palladium acetate, palladium butyrate and palladium acetylacetonate. Preferred palladium compounds include palladium chloride, palladium chloride dihydrate and palladium acetate.

In addition to the Group VIII metal, the catalyst system also contains methyl iodide and lithium iodide, in combination, which serve as promoters for driving the hydrocarbonylation reaction to completion. Applicants have discovered that unexpectedly superior conversion of dimethyl ether to EDDA occurs when lithium acetate is used in conjunction with both lithium iodide and methyl iodide. The amount of lithium iodide and methyl iodide used in conjunction with the desired Group VIII metal catalyst is not critical to practicing the present invention. The collective amount of the iodide components, (i.e., methyl iodide and lithium iodide) can be varied between wide limits.

Reaction time is a convenient control parameter in practicing the present invention and optimum reaction times can be determined based upon the enumerated reaction conditions, catalyst system, and catalyst concentration presented herein. Reaction times required to produce desired amounts of products will also depend upon the reaction temperature and pressure. At constant temperature, pressure, and catalyst concentration, shorter reaction times generally will result in the production of more methyl acetate, acetic anhydride, and acetic acid than EDDA, with very little acetaldehyde. At longer residence times, the production of acetic anhydride decreases significantly, while EDDA and acetic acid production increase significantly. Thus reactor residence time is a useful variable to control product distribution. The reaction is preferably run in the liquid phase containing a high proportion of acetic acid which, as earlier discussed, is a reactant in the present process as well as a coproduct produced therefrom. The liquid also will contain various amounts of the coproducts acetic anhydride, methyl acetate, acetaldehyde, and EDDA. A non-reactive dipolar solvent may be utilized in conjunction with these components.

The reactions which occur in reactor 305 are exothermic, and the heat generated is removed by passing cooling fluid 307, preferably water, through heat exchanger 309 disposed in reactor 305, and withdrawing heated fluid 311, preferably steam, therefrom. Vapor phase reaction products and other volatile components in the reactor overhead are cooled and partially condensed in cooler 313 and flow to separator 315.

Condensate 317 is withdrawn therefrom and returned to reactor 305, and vapor 319 is passed into absorber 321. Cool acetic acid stream 323 passes downward through absorber 321 and absorbs any residual coproducts and volatile catalyst components, rich absorber solvent 324 is combined with acetic acid recycle 325, and combined stream 327 is returned to reactor 305. Absorber overhead stream 31 contains unreacted synthesis gas components and is rich in $CO_2$; a portion 7 thereof is recycled to POX reactor system 101 and the remaining portion 33 is removed as purge to prevent buildup of inert gas components such as argon.

Reactor liquid product stream 328 is flashed across valve 329 and flows into separator 330. Liquid stream 331, containing typically about 10% of the methyl acetate and acetic anhydride in reactor liquid effluent 328 and 15% of the acetic acid in stream 328, is returned to reactor 305. Stream 331 also contains some soluble catalyst components including lithium iodide, lithium acetate, and/or rhodium compounds. The vapor from separator 330 is partially condensed in cooler 333 and flows into separator 335 from which is withdrawn vapor stream 336 comprising DME, methyl iodide promoter, and unreacted synthesis gas components; this vapor stream is compressed by compressor 337 and compressed recycle stream 303 is combined with reactor feed 25.

Liquid 339 from separator 335, comprising EDDA, acetic acid, acetic anhydride, methyl acetate, and the catalyst component methyl iodide, is flashed across valve 341 into distillation column 343. Overhead vapor 344 comprising acetic anhydride, methyl acetate, and methyl iodide is condensed, and a portion 345 of this condensate is combined with catalyst makeup 347 and returned to reactor 305. Another portion 346 of this overhead condensate optionally is withdrawn as a mixed product which can be separated by distillation (not shown) to yield the individual products acetic anhydride and methyl acetate, and methyl iodide which is returned to reactor 305.

Bottoms liquid stream 349 comprising EDDA and acetic acid is further separated in distillation column 351 into acetic acid overhead 353 and crude EDDA bottoms 355 containing EDDA and residual heavier components. The crude EDDA is further purified in distillation column 357 to yield high purity EDDA overhead 27 and heavy residue 359. Optionally, EDDA is pyrolyzed and separated as earlier described and shown in FIG. 1 to yield final vinyl acetate product 35 and acetic acid coproduct 10.

The integrated process described above thus enables the production of desired amounts of acetic acid (HOAc), acetic anhydride ($Ac_2O$), ethylidine diacetate (EDDA), acetaldehyde (AcH), and methyl acetate (MeOAc or MA) from a hydrocarbon feed (preferably natural gas), steam, and oxygen without the need for separate production or import of other intermediate components. The additional product vinyl acetate (VAc) can be produced by pyrolysis of EDDA.

There are three key characteristic features of the present invention: 1) direct coupling of the LP DME and LP OA reactors; 2) integration of these reactors with the POX reactor; and 3) the overall process to produce VAM. These key characteristics are summarized in turn below.

(1) Direct Coupling of the LP DME and LP OA Process Operations

The LP OA process requires a feed stream consisting of DME, $H_2$ and CO. The typical operating conditions for the LP DME process result in the partial conversion of syngas to DME. One of the key advantages of the present invention is that the feed requirement of the LP OA process (stream 25, FIG. 1) matches the typical product stream (stream 19, FIG. 1) from the LP DME process. The conventional production of EDDA, for example, would typically include the production of DME from methanol, recovery [collection and purification] of the DME, and finally addition of DME, $H_2$ and CO to an EDDA reactor. In the preferred mode of the present invention, by contrast, the unreacted $H_2$ and CO in the gaseous DME product stream from the LP DME reactor (which also contains $CO_2$ and methanol) becomes the direct feed to the LP OA reactor to produce EDDA and the other coproducts.

The overall net reaction of the synthesis gas feed components for the production of vinyl acetate (VAc) is $$10\ CO+7\ H_2 \rightarrow VAc+2\ HOAc+2\ CO_2$$

Although this process uses syngas feed in place of more expensive ethylene, it has the disadvantage that it makes 1.4 pounds of HOAc for each pound of VAc produced.

If all of the acetic acid is recycled back to the POX unit and combined with natural gas for syngas generation then the actual overall component balance can be approximated as:

$$5.4\ CH_4+6.3\ O_2 \rightarrow VAc+7.8\ H_2O+1.4\ CO_2$$

If approximately half of the acetic acid is recycled back to the POX unit, the actual overall component balance can be approximated as:

$$6.3\ CH_4+5.9\ O_2 \rightarrow VAc+7.4\ H_2O+0.1\ CO_2+1.1\ HOAc$$

The above equation demonstrates that the carbon balance is very tight if half of the acetic acid is exported as a coproduct. Exporting acetic acid in larger amounts would require that the POX unit be operated on a more carbon-rich feed or that additional hydrogen-rich components (e.g. $H_2$ or MeOH) be exported as coproducts. In such a case, hydrogen would be removed from LP DME reactor feed 13 of FIG. 1.

There are several distinct advantages resulting from the direct coupling of the LP DME and LP OA processes in the present invention compared with existing state-of-the-art technology. These advantages are:

a) EDDA and selected coproducts can be produced directly from readily available and relatively inexpensive synthesis gas. The competing EDDA technologies produce EDDA from more expensive feedstocks including methyl acetate, methanol and DME.

b) There is no requirement for complete syngas conversion to DME. Separate DME production from syngas by known methods requires additional recycle equipment to accomplish nearly total conversion of the feed syngas gas to DME.

c) Direct use of the gaseous LP DME product stream eliminates the additional equipment and utilities required to condense and purify the intermediate DME product.

d) Only minimal purification of the methanol byproduct stream is required prior to the optional recycling of this liquid byproduct back to the LP DME reactor where it is converted to additional DME.

There are several possible variations to the process within the scope of the present invention. These variations impart flexibility and utility to the process, and can be used for various applications depending on the desired mix of products and available feedstocks. Several of these variations are described in the alternate embodiments described below:

a) The LP DME process is very flexible with respect to byproduct methanol production vs. methanol recycle to the DME reactor. Although the process as described above recycles and consumes all of the byproduct methanol, the process could alternatively produce an exportable methanol product stream or consume excess imported methanol with the feed gas for DME production. This flexibility allows the same installed process equipment to take advantage of the variable market price for methanol. Methanol could be exported during the periods of higher methanol prices and imported during periods of lower methanol prices.

b) The EDDA and acetic acid products are recovered from the LP OA reactor, and other intermediate products are recycled to the reactor along with some of the acetic acid. Alternatively, these other intermediate products can be recovered separately as final products, including methyl acetate, DME, acetaldehyde, and acetic anhydride. Methyl acetate is a particularly favorable coproduct due to its relatively high concentration in the reactor effluent. This potentially wide product slate from the process is a key advantage of the present invention.

c) As illustrated by the Examples below, the LP OA reactions are enhanced by the presence of $CO_2$ in the reactor feed, particularly when methanol is present, and the EDDA reaction may partially catalyze the reverse water gas shift reaction between $CO_2$ and $H_2$ in the feed gas. This reaction ultimately consumes a fraction of the DME, $H_2$, CO and $CO_2$ in the feed gas to produce additional acetyl compounds. An optimized version of this process may include an additional processing step between the LP DME and the LP OA reactors to reduce the concentration of $CO_2$ in the LP OA reactor feed gas.—Alternatively, additional $CO_2$ can be added to the reactor feed gas. The added cost and complexity of this additional equipment could be partially offset by higher yields in the LP OA process. Including this step to modify the LP OA feed gas composition would not substantially change the nature of the LP DME and LP OA reactor integration.

(2) Coupling EDDA Production With Syngas Generation

POX reactors for syngas generation have the flexibility to operate on a wide variety of hydrocarbon feeds and often require the use of a diluent stream (typically steam or $CO_2$) to moderate the reaction combustion temperature. If $CO_2$ is used as the moderant, it can partially react with the available $H_2$ to produce additional CO through the reverse water-gas-shift reaction and thus increase overall carbon utilization.

These characteristics provide a unique opportunity to recycle the coproduct and waste streams from the EDDA production step and convert them into valuable feed streams. Several key advantages which result from the integration of the EDDA synthesis and the POX syngas reactor include:

a) The excess coproduct acetic acid can be used in combination with natural gas as the feed to the POX reactor. This eliminates the need to export excessive quantities of acetic acid and provides a method to maintain the carbon balance of the integrated process since acetic acid is more carbon-rich than natural gas. This integration provides the means to operate the facility in an EDDA-only production mode.

b) The use of excess $CO_2$ vs. steam to moderate POX reactor temperature eliminates the need to import steam in the POX reactor.

c) The use of excess $CO_2$ vs. steam to moderate POX reactor temperature also provides a better carbon utilization. Without this integration, the LP OA reactor offgas would be a waste stream that would be incinerated and vented to the atmosphere. These $CO_2$ molecules are instead converted to synthesis gas which reduces the natural gas feed requirement. The recycled $CO_2$ forms water and CO via the reverse water gas shift reaction in the POX reactor and as a result the waste streams from this process are largely water. This is a clear advantage over emitting a $CO_2$-rich vent stream, since $CO_2$ is considered a greenhouse gas.

d) Recycling unreacted syngas from the LP OA reactor eliminates the need to achieve high syngas conversions per pass. Since the unconverted syngas is largely returned to the process, it is possible to operate the LP OA reactor with an excess of syngas which improves the conversion kinetics of the more valuable DME feed. These improved kinetics ultimately result in a smaller reactor size.

The process as described above maintains an overall carbon balance by recycling nearly all of the acetic acid coproduced in the LP OA reactor. Two other optional methods to maintain or improve the overall carbon balance are to utilize a more carbon-rich POX feed in place of natural gas, and to remove excess hydrogen from LP DME feed (stream 13, FIG. 1). This hydrogen could be a high value coproduct and would enable the production and export of more acetic acid. This modification to the process would add flexibility and would not substantially change the nature of the present invention.

(3) Overall Integrated Vinyl Acetate Process Scheme

Most of the VAc currently produced is manufactured either by the acetic acid/ethylene route or by the pyrolysis of EDDA. VAc produced by the acetic acid/ethylene route requires expensive feedstocks while VAc produced by EDDA pyrolysis yields an equimolar amount of acetic acid. The process of the present invention avoids both of these disadvantages. VAM is produced from inexpensive natural gas (or other inexpensive hydrocarbon feedstocks) and the process has the ability to recycle all of the coproduced acetic acid. By having the ability to operate with varying levels of acetic acid recycle, the process operator can vary the amount of acetic acid export to meet market demand.

In addition to converting excess acetic acid into additional syngas, the POX reactor has the capability to convert most of the other small waste and byproduct streams in the overall integrated process to additional syngas feed. This characteristic has both environmental and economic advantages. As a result, the largest waste stream besides coproduced water is the gaseous purge from LP OA offgas which is required to prevent excessive buildup of inert argon and nitrogen gases in the syngas from the POX reactor.

The following examples are presented to further illustrate the scope of the present invention.

EXAMPLE 1

A 300 cc Hastelloy C autoclave was equipped with a dip tube for loading DME from a preweighed cylinder, a thermocouple, cooling coils, a belt driven magnetic stirrer, and an inlet for gases. The autoclave was protected from overpressure by a rupture disk and a relief valve. All inlet lines, valves and other surfaces being exposed to methyl iodide were made of either Hastelloy C or Inconel. The working volume of the autoclave was approximately 283 cc.

The following general procedure was used to load, pressurize, run, and unload the autoclave. The autoclave was cooled for 30 minutes by filling with dry ice, the dry ice was removed, and the autoclave was charged with acetic acid, lithium iodide, methyl iodide, optionally lithium acetate, the Group VIII metal component rhodium chloride, and other components given in Tables 1, 3 and 5. The autoclave was sealed, pressurized with nitrogen to test for leaks, vented, pressurized with a premixed synthesis gas containing 70 vol % CO/30% vol % $H_2$ at least thrice, and vented to approximately 20 psi. DME was transferred to the autoclave from a preweighed cylinder. While stirring, the syngas pressure was increased to 300–400 psi from a ballast. The ballast pressure was recorded and the reactor was heated to operating temperature. At operating temperature, reactor pressure was increased to operating pressure from the ballast. The reactions were carried out for the desired length of time while the autoclave was maintained at constant pressure. Following completion of the reaction, the autoclave was cooled to room temperature and a valve leading to a flash pot capture cylinder (500 cc) was opened. The autoclave contents were flashed into the capture cylinder and the resulting pressure was recorded. The flash liquid and vapor in the capture cylinder were analyzed by gas chromatography using a DB-1701 FSOT capillary column interfaced to a flame ionization detector. Quantitation was obtained using an internal standard technique, and the lower detection limit for the compounds of interest was approximately 0.002 wt.%. All organic compound structures were verified by gas chromatography/mass spectrometry (GC/MS).

The operating conditions, feed component weights, and flash liquid component weights are summarized in Table 1.

TABLE 1

Results of Autoclave Run No. 1

| Reaction Conditions: | Temperature | 374° F. |
| --- | --- | --- |
|  | Pressure | 1443 psig |
|  | Reaction time | 90 min |

| Component | Weight, grams | |
| --- | --- | --- |
|  | Initial Reactor Charge | Flash Pot Liquid |
| Carbon dioxide | 8.00 | — |
| Dimethyl ether | 19.00 | 0.31 |
| Methanol | 2.11 | — |
| Water | 0.33 | — |
| Acetic acid | 129.44 | 147.90 |
| Ethylidene diacetate | — | 10.38 |
| Acetaldehyde | — | 0.08 |
| Methyl acetate | — | 18.62 |
| Acetic anhydride | 13.91 | 4.10 |
| Methyl iodide | 8.48 | 5.42 |
| Lithium iodide | 1.50 | — |
| Rhodium chloride | 0.30 | — |
| Lithium acetate | 0.99 | — |
| Total weight, grams | 184.06 | 194.80 |

These experimental data were used with predicted phase equilibria and material balances to calculate the vapor and liquid compositions for the charged and heated reactor at initial reaction conditions, the reactor at final reaction conditions, and the flash pot at ambient temperature. The results of the calculations are summarized in Table 2 and indicate the relative distribution of components between the vapor and liquid phases. DME conversions to the various coproduct components are also given in Table 2.

TABLE 2

Calculated Liquid and Vapor Compositions for Run No. 1

|  | Initial Rxn. Conditions | | Final Rxn. Conditions | | Flash Pot Split | |
| --- | --- | --- | --- | --- | --- | --- |
|  | Liquid | Vapor | Liquid | Vapor | Liquid | Vapor |
| Temperature (°F.) | 374 | 374 | 374 | 374 | 77 | 77 |
| Pressure (psia) | 1458 | 1458 | 1458 | 1458 | 263 | 263 |
| Volume (cc) | 236.1 | 46.9 | 244.6 | 38.4 |  |  |
| Total Charge |  |  |  |  |  |  |
| (grams) | 181.2 | 4.1 | 197.1 | 1.8 | 194.4 | 8.5 |
| (mgmoles) | 3098 | 129 | 3124 | 96 | 2985 | 434 |
| Composition | (wt %) | (mol %) | (wt %) | (mol %) | (wt %) | (mol %) |
| Hydrogen | 0.03 | 21.75 | 0.07 | 57.46 | 0.002 | 41.32 |
| Carbon Monoxide | 1.46 | 33.52 | 0.68 | 19.35 | 0.130 | 45.27 |
| Carbon Dioxide | 3.87 | 17.23 | 2.31 | 13.18 | 1.37 | 12.87 |
| Dimethyl Ether | 9.92 | 17.02 | 0.17 | 0.28 | 0.16 | 0.14 |
| Methanol | 1.14 | 0.94 | 0 | 0 | 0 | 0 |
| Water | 0.18 | 0.18 | 0 | 0 | 0 | 0 |
| Acetic Acid | 71.15 | 6.84 | 74.91 | 5.29 | 76.08 | 0.0213 |
| Ethylidene diacetate |  |  | 5.34 | 0.11 | 5.42 | 0.0007 |
| Acetaldehyde |  |  | 0.05 | 0.04 | 0.05 | 0.0064 |

TABLE 2-continued

| | | | | | | |
|---|---|---|---|---|---|---|
| Methyl Acetate | | | 9.95 | 2.62 | 10.15 | 0.1962 |
| Acetic Anhydride | 7.64 | 0.55 | 2.26 | 0.12 | 2.30 | 0.0005 |
| Methyl Iodide | 4.60 | 0.80 | 4.26 | 0.64 | 4.34 | 0.07 |
| Total Collected Weight of Liq + Vap + Cat (grams) | 188.0 | | 201.7 | | 200.9 | |
| DME Conversions, %: | | | | | | |
| Ethylidene diacetate | 35.00 | | | | | |
| Methyl Acetate | 64.79 | | | | | |
| Acetic Anhydride | −22.41 | | | | | |
| Acetaldehyde | 0.53 | | | | | |
| From $CO_2$ Shift | 15.87 | | | | | |
| From Water | 4.44 | | | | | |
| Total Percent Conversion | 98.22 | | | | | |

Average Productivities: 4.52 mol DME/(mol $CH_3I$.hr)
0.81 mol EDDA/(mol $CH_3I$.hr)

The calculated dimethyl ether conversion was 4.52 mol DME per mole methyl iodide per hour, and the EDDA reactor productivity was 0.81 mole EDDA per mole methyl iodide catalyst per hour. The addition of carbon dioxide, methanol, and water to the reactor feed simulates the direct flow of LP DME reactor effluent into the LP EDDA reactor without intermediate methanol or water removal, and confirms that EDDA synthesis can be carried out successfully under these conditions. Acetic anhydride, an intermediate product of EDDA synthesis, can be recycled to the reactor where it becomes an intermediate reactant for additional EDDA synthesis. Acetic acid, which is added to the reactor as the main component of the liquid phase, is both a reactant and a net product in the overall reaction mechanism.

EXAMPLE 2

The procedure of Example 1 was utilized to test the reaction characteristics at a lower pressure (1007 psig) and a shorter reaction time (45 min) using different amounts of catalyst charge. The results are summarized in Table 3.

TABLE 3

Results of Autoclave Run No. 2

| Reaction Conditions: | Temperature | 374° F. |
|---|---|---|
| | Pressure | 1007 psig |
| | Reaction time | 45 min |

| | Weight, grams | |
|---|---|---|
| Component | Initial Reactor Charge | Flash Liquid |
| Carbon dioxide | 4.50 | — |

TABLE 3-continued

| Dimethyl ether | 20.96 | 3.36 |
|---|---|---|
| Methanol | 0.74 | — |
| Water | 0.07 | — |
| Acetic acid | 128.90 | 147.34 |
| Ethylidene diacetate | — | 4.95 |
| Acetaldehyde | — | 0.04 |
| Methyl acetate | — | 22.06 |
| Acetic anhydride | 17.51 | 8.38 |
| Methyl iodide | 12.97 | 7.50 |
| Lithium iodide | 1.50 | — |
| Rhodium chloride | 0.40 | — |
| Lithium acetate | 1.99 | — |
| Total weight, grams | 189.54 | 196.30 |

These experimental data were used with predicted phase equilibria and material balances to calculate the vapor and liquid compositions for the charged and heated reactor at initial reaction conditions, the reactor at final reaction conditions, and the flash pot at ambient temperature. The results of the calculations are summarized in Table 4 and indicate the relative distribution of components between the vapor and liquid phases. DME conversions to the various coproduct components are also given in Table 4.

TABLE 4

Calculated Liquid and Vapor Compositions for Run No. 2

|  | Initial Rxn. Conditions | | Final Rxn. Conditions | | Flash Pot Split | |
|---|---|---|---|---|---|---|
|  | Liquid | Vapor | Liquid | Vapor | Liquid | Vapor |
| Temperature (°F.) | 374 | 374 | 374 | 374 | 77 | 77 |
| Pressure (psia) | 1022 | 1022 | 1022 | 1022 | 177 | 177 |
| Volume (cc) | 242.9 | 40.1 | 248.8 | 34.3 |  |  |
| Total Charge |  |  |  |  |  |  |
| (grams) | 185.4 | 2.7 | 197.4 | 1.3 | 196.1 | 5.5 |
| (mgmoles) | 3037 | 78 | 3077 | 61 | 2988 | 289 |
| Composition | (wt %) | (mol %) | (wt %) | (mol %) | (wt %) | (mol %) |
| Hydrogen | 0.02 | 20.09 | 0.04 | 50.88 | 0.001 | 39.60 |
| Carbon Monoxide | 0.93 | 29.56 | 0.74 | 28.23 | 0.111 | 54.73 |
| Carbon Dioxide | 2.18 | 13.06 | 0.36 | 2.80 | 0.21 | 2.92 |
| Dimethyl Ether | 10.82 | 24.17 | 1.78 | 4.02 | 1.71 | 2.10 |
| Methanol | 0.39 | 0.41 | 0 | 0 | 0 | 0 |
| Water | 0.04 | 0.05 | 0 | 0 | 0 | 0 |
| Acetic Acid | 69.30 | 8.17 | 72.32 | 6.73 | 72.94 | 0.0277 |
| Ethylidene diacetate |  |  | 2.51 | 0.06 | 2.53 | 0.0004 |
| Acetaldehyde |  |  | 0.02 | 0.02 | 0.02 | 0.0041 |
| Methyl Acetate |  |  | 11.47 | 3.81 | 11.61 | 0.2824 |
| Acetic Anhydride | 9.41 | 0.82 | 4.25 | 0.30 | 4.29 | 0.0013 |
| Methyl Iodide | 6.90 | 1.50 | 6.51 | 1.28 | 6.59 | 0.14 |
| Total Collected Weight of Liq + Vap + Cat (grams) | 192.0 |  | 202.6 |  | 202.3 |  |
| DME Conversions, %: |  |  |  |  |  |  |
| Ethylidene diacetate | 14.92 |  |  |  |  |  |
| Methyl Acetate | 67.70 |  |  |  |  |  |
| Acetic Anhydride | −19.60 |  |  |  |  |  |
| Acetaldehyde | 0.23 |  |  |  |  |  |
| From CO$_2$ Shift | 18.57 |  |  |  |  |  |
| From Water | 0.85 |  |  |  |  |  |
| Total Percent Conversion | 82.67 |  |  |  |  |  |

Average Productivities: 5.49 mol DME/(mol CH$_3$I.hr)
0.50 mol EDDA/(mol CH$_3$I.hr)

The calculated dimethyl ether conversion was 5.49 mol DME per mole methyl iodide catalyst per hour and the EDDA reactor productivity was 0.50 mole EDDA per mole methyl iodide per hour. The addition of carbon dioxide, methanol, and water to the reactor feed again confirmed that EDDA synthesis can be carried out successfully using LP DME reactor effluent as direct feed to the EDDA reactor.

EXAMPLE 3

The procedure of Example 2 was utilized to test the reaction characteristics when the intermediate product methyl acetate was added to the feed to simulate recycle of this component to the reactor. The results are summarized in Table 5 below.

TABLE 5

Results of Autoclave Run No. 3

| Reaction Conditions: | Temperature | 374° F. |
|---|---|---|
|  | Pressure | 989 psig |
|  | Reaction time | 45 min |

| | Weight, grams | |
|---|---|---|
| Component | Initial Reactor Charge | Flash Liquid |
| Carbon dioxide | 5.47 | ??? |
| Dimethyl ether | 25.40 | 11.29 |
| Methanol | 0.70 | — |
| Water | 0.05 | — |
| Acetic acid | 115.00 | 135.04 |
| Ethylidene diacetate | — | 3.56 |
| Acetaldehyde | — | 0.57 |
| Methyl acetate | 14.96 | 31.58 |
| Acetic anhydride | 14.10 | 7.98 |
| Methyl iodide | 13.00 | 9.27 |
| Lithium iodide | 1.50 | — |
| Rhodium chloride | 0.40 | — |
| Lithium acetate | 2.06 | — |
| Total weight, grams | 192.64 | 198.00 |

These experimental data were used with predicted phase equilibria and material balances to calculate the vapor and liquid compositions for the charged and heated reactor at initial reaction conditions, the reactor at final reaction conditions, and the flash pot at ambient temperature. The results of the calculations are summarized in Table 4 and indicate the relative distribution of components between the vapor and liquid phases. DME conversions to the various coproduct components are also given in Table 6.

Example 2, but indicates that recycle of methyl acetate is feasible.

EXAMPLE 4

Material balances were prepared for the production of vinyl acetate (VAc) at a rate of 755 lb moles/hour according to the embodiment of FIG. 1 using natural gas as feed to the partial oxidation (POX) synthesis gas reactor 101. In a first

TABLE 6

Calculated Liquid and Vapor Compositions for Run No. 3

|  | Initial Rxn. Conditions | | Final Rxn. Conditions | | Flash Pot Split | |
| --- | --- | --- | --- | --- | --- | --- |
|  | Liquid | Vapor | Liquid | Vapor | Liquid | Vapor |
| Temperature (°F.) | 374 | 374 | 374 | 374 | 77 | 77 |
| Pressure (psia) | 1004 | 1004 | 1004 | 1004 | 199 | 199 |
| Volume (cc) | 236.9 | 46.1 | 242.5 | 40.5 |  |  |
| Total Charge |  |  |  |  |  |  |
| (grams) | 187.0 | 3.7 | 197.3 | 2.3 | 195.2 | 7.6 |
| (mgmoles) | 3053 | 95 | 3111 | 76 | 3015 | 333 |
| Composition | (wt %) | (mol %) | (wt %) | (mol %) | (wt %) | (mol %) |
| Hydrogen | 0.02 | 14.91 | 0.03 | 35.77 | 0.001 | 32.24 |
| Carbon Monoxide | 0.74 | 22.76 | 0.66 | 24.14 | 0.120 | 50.96 |
| Carbon Dioxide | 2.54 | 17.21 | 1.20 | 10.02 | 0.66 | 9.73 |
| Dimethyl Ether | 12.87 | 30.43 | 5.90 | 14.27 | 5.71 | 6.44 |
| Methanol | 0.37 | 0.44 | 0 | 0 | 0 | 0 |
| Water | 0.03 | 0.04 | 0 | 0 | 0 | 0 |
| Acetic Acid | 61.24 | 8.35 | 63.96 | 7.30 | 64.79 | 0.0243 |
| Ethylidene diacetate |  |  | 1.73 | 0.06 | 1.75 | 0.0003 |
| Acetaldehyde |  |  | 0.33 | 0.37 | 0.33 | 0.0568 |
| Methyl Acetate | 7.87 | 3.45 | 15.80 | 6.25 | 16.09 | 0.3961 |
| Acetic Anhydride | 7.50 | 0.76 | 3.87 | 0.34 | 3.92 | 0.0012 |
| Methyl Iodide | 6.83 | 1.64 | 6.51 | 1.48 | 6.62 | 0.15 |
| Total Collected Weight of Liq + Vap + Cat (grams) | 194.7 |  | 203.5 |  | 202.5 |  |
| DME Conversions, %: |  |  |  |  |  |  |
| Ethylidene diacetate | 8.49 |  |  |  |  |  |
| Methyl Acetate | 40.55 |  |  |  |  |  |
| Acetic Anhydride | −11.44 |  |  |  |  |  |
| Acetaldehyde | 2.71 |  |  |  |  |  |
| From CO$_2$ Shift | 11.40 |  |  |  |  |  |
| From Water | 0.50 |  |  |  |  |  |
| Total Percent Conversion | 52.22 |  |  |  |  |  |

Average Productivities: 4.19 mol DME/(mol CH$_3$I.hr)
0.34 mol EDDA/(mol CH$_3$I.hr)

The calculated dimethyl ether conversion was 4.19 mole DME per mole methyl iodide catalyst per hour and the EDDA reactor productivity was 0.34 mole EDDA per mole methyl iodide per hour. The addition of carbon dioxide, methanol, and water to the reactor feed again confirmed that EDDA synthesis can be carried out successfully using LP DME reactor effluent as direct feed to the EDDA reactor without the need for intermediate separation steps. The addition of methyl acetate to the feed to simulate recycle of this intermediate compound may have been a factor in the reduced EDDA reactor productivity compared with material balance, 50% of the total acetic acid stream 43 was taken as product 10 and the remainder 9 was sent to POX reactor 101 to generate additional synthesis gas. Table 7 summarizes the stream conditions and properties for the 50% recycle case, and shows that a natural gas feed rate (as methane) of 4790 lb moles/hour is required to produce 755 lb moles/hr of vinyl acetate with a coproduct acetic acid rate of 804 lb moles/hr. A second material balance was prepared for the recycle of 100% of the acetic acid to the POX reaction system for the same vinyl acetate production rate of 755 lb moles/hour as summarized in Table 8.

TABLE 7

Material Balance for 50% Acetic Acid Recycle

| Material Balance Point | 1 | 5 | 7 | 9 | 10 | 11 | 13 | 19 | 21 |
| --- | --- | --- | --- | --- | --- | --- | --- | --- | --- |

TABLE 7-continued

Material Balance for 50% Acetic Acid Recycle

| | | | | | | | | | |
|---|---|---|---|---|---|---|---|---|---|
| Temperature (°F.) | 80 | 80 | 100 | 100 | 100 | 100 | 100 | 280 | 170 |
| Pressure (psia) | 1250 | 1250 | 1050 | 1250 | 20 | 1200 | 1200 | 1150 | 20 |
| Average Molecular Wt. | 16.0 | 32.0 | 36.1 | 60.1 | 60.1 | 18.0 | 22.0 | 33.0 | 32.0 |
| Component (mol/hr) | | | | | | | | | |
| Hydrogen | | | 848 | | | | 6557 | 1629 | |
| Carbon Monoxide | | | 905 | | | | 8663 | 4050 | |
| Carbon Dioxide | | | 4244 | | | | 2942 | 4375 | |
| Argon | | 23 | 737 | | | | 760 | 760 | |
| Oxygen | | 4543 | | | | | | | |
| Methanol | | | | | | | | 462 | 385 |
| Water | | | | | | 5567 | | 118 | |
| Methane | 4790 | | 27 | | | | 28 | 28 | |
| Dimethyl Ether | | | 30 | | | | | 1551 | |
| Acetic Acid | | | | 804 | 804 | | | | |
| EDDA | | | | | | | | | |
| VAc | | | | | | | | | |
| Total lbmol/hr | 4790 | 4565 | 6791 | 804 | 804 | 5567 | 18950 | 12974 | 385 |

| Material Balance Point | 22 | 23 | 25 | 27 | 29 | 31 | 33 | 39 | 41 |
|---|---|---|---|---|---|---|---|---|---|
| Temperature (°F.) | 170 | 100 | 100 | 100 | 100 | 100 | 100 | 100 | 100 |
| Pressure (psia) | 20 | 20 | 1150 | 20 | 20 | 1050 | 1050 | 15 | 15 |
| Average Molecular Wt. | 32.0 | 18.0 | 33.2 | 146.1 | 60.1 | 36.1 | 36.1 | 60.1 | 86.1 |
| Component (mol/hr) | | | | | | | | | |
| Hydrogen | | | 1629 | | | 874 | 26 | | |
| Carbon Monoxide | | | 4050 | | | 933 | 28 | | |
| Carbon Dioxide | | | 4375 | | | 4375 | 131 | | |
| Argon | | | 760 | | | 760 | 23 | | |
| Oxygen | | | | | | | | | |
| Methanol | 384 | | 77 | | | | | | |
| Water | | 108 | 10 | | | | | | |
| Methane | | | 28 | | | 28 | 0.8 | | |
| Dimethyl Ether | | | 1551 | | | 31 | 0.9 | | |
| Acetic Acid | | | | | 852 | | | 755 | |
| EDDA | | | | 755 | | | | | |
| VAc | | | | | | | | | 755 |
| Total lbmol/hr | 384 | 108 | 12481 | 755 | 852 | 7001 | 210 | 755 | 755 |

TABLE 8

Material Balance for 100% Acetic Acid Recycle

| Material Balance Point | 1 | 5 | 7 | 9 | 10 | 11 | 13 | 19 | 21 |
|---|---|---|---|---|---|---|---|---|---|
| Temperature (°F.) | 80 | 80 | 100 | 100 | 100 | 100 | 100 | 280 | 170 |
| Pressure (psia) | 1250 | 1250 | 1200 | 1250 | 20 | 1200 | 1200 | 1150 | 20 |
| Average Molecular Wt. | 16.0 | 32.0 | 34.9 | 60.1 | 60.1 | 18.0 | 21.1 | 32.3 | 32.0 |
| Component (mol/hr) | | | | | | | | | |
| Hydrogen | | | 813 | | | | 6697 | 1769 | |
| Carbon Monoxide | | | 748 | | | | 8663 | 4050 | |
| Carbon Dioxide | | | 3450 | | | | 2870 | 4303 | |
| Argon | | 23 | 92 | | | | 115 | 115 | |
| Oxygen | | 4532 | | | | | | | |
| Methanol | | | | | | | | 462 | 385 |
| Water | | | | | | 5548 | | 118 | |
| Methane | 4077 | | 22 | | | | 28 | 28 | |
| Dimethyl Ether | | | 25 | | | | | 1551 | |
| Acetic Acid | | | | 1607 | 0 | | | | |
| EDDA | | | | | | | | | |
| VAc | | | | | | | | | |
| Total lbmol/hr | 4077 | 4555 | 5151 | 1607 | 0 | 5548 | 18373 | 12396 | 385 |

| Material Balance Point | 22 | 23 | 25 | 27 | 29 | 31 | 33 | 39 | 41 |
|---|---|---|---|---|---|---|---|---|---|

TABLE 8-continued

Material Balance for 100% Acetic Acid Recycle

| | | | | | | | | | |
|---|---|---|---|---|---|---|---|---|---|
| Temperature (°F.) | 170 | 100 | 100 | 100 | 100 | 100 | 100 | 100 | 100 |
| Pressure (psia) | 20 | 20 | 1150 | 20 | 20 | 1050 | 1050 | 15 | 15 |
| Average Molecular Wt. | 32.0 | 18.0 | 32.4 | 146.1 | 60.1 | 34.9 | 34.9 | 60.1 | 86.1 |
| Component (mol/hr) | | | | | | | | | |
| Hydrogen | | | 1769 | | | 1014 | 201 | | |
| Carbon Monoxide | | | 4050 | | | 933 | 185 | | |
| Carbon Dioxide | | | 4303 | | | 4303 | 853 | | |
| Argon | | | 115 | | | 115 | 23 | | |
| Oxygen | | | | | | | | | |
| Methanol | 384 | | 77 | | | | | | |
| Water | | 108 | 10 | | | | | | |
| Methane | | | 28 | | | 28 | 5.5 | | |
| Dimethyl Ether | | | 1551 | | | 31 | 6.1 | | |
| Acetic Acid | | | | | 852 | | | 755 | |
| EDDA | | | | 755 | | | | | |
| VAc | | | | | | | | | 755 |
| Total lbmol/hr | 384 | 108 | 11903 | 755 | 852 | 6424 | 1273 | 755 | 755 |

It is seen from Tables 7 and 8 that the required natural gas feed rate is reduced by 713 lb moles/hour or 15% by recycling the additional acetic acid coproduct to the POX reactor. Thus the recycle of acetic acid to the POX reactor for conversion into additional synthesis gas is a useful alternative when there is no market for the coproduct acetic acid.

EXAMPLE 5

Additional experiments were carried out to investigate the effect of $CO_2$ on the hydrocarbonylation reactions. The methods and apparatus described in Example 1 were used; liquid reactants and catalysts were charged to the reactor and the autoclave was flushed with nitrogen once and syngas of the appropriate composition twice. Dimethyl ether was charged and the reactor pressurized to 400 psig with syngas or alternatively to 100 psig with $CO_2$ followed by syngas up to 400 psig. In some experiments, $CO_2$ was charged by weight from a weighed cylinder. The temperature was increased to the operating temperature of 190° C. and the operating pressure was increased and maintained at 1500 psig. After the reaction was complete, the autoclave was depressurized and cooled to ambient conditions. The reaction liquid was isolated and the autoclave was rinsed with 25 ml of acetic acid. The reaction liquid and rinse were combined and analyzed by gas chromatography.

Six experiments were carried out using a syngas composition of 80 mol % CO and 20 mol % hydrogen to compare the effect of added $CO_2$ with and without the catalyst component lithium acetate (LiOAc). The results are given in Table 9. Acetyl yield is defined on a molar basis as the sum of all the observed acetyl products divided by the charged DME. The acetyl products include primarily acetaldehyde (denoted as AcH), methyl acetate (MA), ethyl iodide (EtI), ethyl acetate (EtOAc), acetic anhydride ($Ac_2O$), and ethylidene diacetate (EDDA). Formation of EDDA requires two moles of DME. It is seen from experiments 1–3 and 4–6 that the addition of $CO_2$ has a significant effect on the overall acetyl product yield as well as the individual acetyl product selectivities. This finding was unexpected, since none of the prior art teaches that $CO_2$ influences the product yield and selectivity. Some of the prior art earlier cited, specifically U.S. Pat. Nos. 4,810,821 and 5,117,046, actually teach that $CO_2$ is an inert diluent which does not react with other components present in such a reaction system.

TABLE 9

Effect of $CO_2$ on Hydrocarbonylation of DME to Acetyls[1]
(Example 5)

| Expt. No. | Catalyst, mmol | | | Feed, mmol[2] | | Acetyl Yield % | Molar Selectivity, % | | | |
|---|---|---|---|---|---|---|---|---|---|---|
| | MeI | LiI | LiOAc | DME | $CO_2$ | | MA | EtOAc | $Ac_2O$ | EDDA |
| 1 | 63.4 | 11.2 | 0 | 145.6 | 0 | 70.2 | 10.7 | 0.7 | 63.9 | 24.7 |
| 2 | 69.4 | 11.2 | 0 | 154.3 | 100.0 | 92.4 | 26.9 | 0.2 | 57.2 | 15.6 |
| 3 | 63.4 | 11.2 | 0 | 136.9 | 156.8 | 79.9 | 54.2 | trace | 34.8 | 10.9 |
| 4 | 63.7 | 11.2 | 12.1 | 139.0 | 0 | 70.6 | 12.9 | 0.4 | 66.9 | 19.8 |
| 5 | 63.4 | 11.2 | 12.1 | 154.3 | 56.8 | 83.1 | 27.7 | 0.1 | 61.9 | 10.3 |
| 6 | 63.4 | 11.2 | 12.1 | 123.9 | 156.8 | 83.7 | 22.9 | 0.2 | 62.5 | 14.5 |

[1]Syngas feed 80% CO/20% $H_2$ (molar); total pressure 1500 psig; temperature 190° C.
[2]0.2 g $RhCl_3.3H_2O$ and 135 ml acetic acid added.

Experiments 1–3, in which lithium acetate was not used as a catalyst component, show that the addition of increasing amounts of $CO_2$ as a reactant significantly increases the product selectivity to methyl acetate while reducing the selectivity to acetic anhydride and EDDA. Overall yield of acetyl compounds passes through a maximum between zero and 156.8 mmol added $CO_2$, and is always higher than with reactor operation using syngas containing no $CO_2$. Experiments 4–6, in which lithium acetate was included as a catalyst component, show similar effects of $CO_2$ addition although selectivity to acetic anhydride is not decreased significantly.

EXAMPLE 6

The experiments of Example 5 were repeated except that a syngas containing 50 mol % CO and 50 mol % hydrogen was used. Results are given in Table 10. Without lithium acetate as a catalyst, overall acetyl yield increased significantly as $CO_2$ was added in experiments 7–9, reaching 96.5% in experiment 9. Decreases in selectivity for acetic anhydride and EDDA were minimal compared with experiments 1–3. When lithium acetate is used as a catalyst component in experiments 10–12, acetyl yield changed only slightly, while EDDA selectivity decreased significantly and methyl acetate selectivity increased significantly.

The results of experiments 7–12 confirm the unexpected findings of experiments 1–6, namely, that the addition of $CO_2$ to a reaction system containing dimethyl ether, CO, and hydrogen has a significant effect on product yield and selectivity. The selection of catalyst components and the amount of $CO_2$ added can be used to improve overall product yield and change the selectivity of specific product components. Acetyl yield is increased over that obtained from syngas containing no $CO_2$ by adding $CO_2$ such that the molar ratio of $CO_2$ to DME in the reactor feed is between 0.3 and 1.3.

EXAMPLE 7

The previous experiments were repeated with methanol added as a reactant to determine the combined effect of $CO_2$ and methanol on product yield and selectivity. These experi-

TABLE 10

Effect of $CO_2$ on Hydrocarbonylation of DME to Acetyls[1]
(Example 6)

| Expt. No. | Catalyst, mmol | | | Feed, mmol[2] | | Acetyl Yield % | Molar Selectivity, % | | | |
|---|---|---|---|---|---|---|---|---|---|---|
| | MeI | LiI | LiOAc | DME | $CO_2$ | | MA | EtOAc | $Ac_2O$ | EDDA |
| 7 | 63.4 | 11.2 | 0 | 121.7 | 0 | 84.4 | 17.4 | 0.9 | 23.1 | 58.5 |
| 8 | 69.4 | 11.2 | 0 | 150.0 | 88.6 | 84.1 | 30.6 | 0.5 | 23.9 | 45.0 |
| 9 | 63.4 | 11.4 | 0 | 121.7 | 106.8 | 96.5 | 30.2 | 0.5 | 22.2 | 47.1 |
| 10 | 63.7 | 11.4 | 12.1 | 141.3 | 0 | 77.6 | 22.4 | 0.6 | 15.8 | 61.1 |
| 11 | 63.4 | 11.2 | 12.1 | 147.8 | 93.2 | 73.0 | 41.9 | 0.2 | 31.8 | 26.1 |
| 12(3) | 63.4 | 11.2 | 12.1 | 152.2 | 293.2 | 75.0 | 55.4 | 1.0 | 15.8 | 27.5 |

[1]Syngas feed 50% CO/50% $H_2$ (molar); total pressure 1500 psig; temperature 190° C.
[2]0.2 g $RhCl_3.3H_2O$ and 135 ml acetic acid added.
[3]Molar selectivity of acetaldehyde (AcH) in experiment 12 was 0.3%

The results of experiments 1–12 are compared in Table 11 in order to observe the effect of the $CO_2$/DME molar ratio on acetyl yield. The addition of $CO_2$ to the reactor feed in a preferred $CO_2$/DME molar ratio range of 0.3–1.3 generally increases the overall acetyl product yield. This indicates unexpectedly that the $CO_2$ is affecting product yield, because if the $CO_2$ were merely a diluent the acetyl product yield would decrease due to lower reactant partial pressures. As observed earlier, the addition of $CO_2$ in this preferred range also unexpectedly changes the selectivities of the various individual acetyl products.

TABLE 11

Effect of $CO_2$/DME Molar Ratio on Acetyl Yield

| Exp. No. | $CO_2$/DME Molar Ratio | Acetyl Yield, % |
|---|---|---|
| 1 | 0 | 70.2 |
| 2 | 0.65 | 92.4 |
| 3 | 1.15 | 79.9 |
| 4 | 0 | 70.6 |
| 5 | 0.37 | 83.1 |
| 6 | 1.27 | 83.7 |
| 7 | 0 | 84.4 |
| 8 | 0.59 | 84.1 |
| 9 | 0.88 | 96.5 |
| 10 | 0 | 77.6 |
| 11 | 0.63 | 73.0 |
| 12 | 1.93 | 75.0 | ments simulate the operation of liquid phase acetyl reactor in which the feed for LP acetyl reactor system 301 is provided directly from liquid phase dimethyl ether reactor system 201. LP DME reactor effluent 19 contains dimethyl ether, methanol, hydrogen, CO, and $CO_2$, and is used directly as feed to reactor system 301 in a preferred embodiment of the invention. As seen in the results of Table 12, the addition of $CO_2$ gave completely different unexpected results than the similar experiments of Examples 5 and 6 in which methanol was not present in the feed. The data from experiments 13–15, in which the DME/MeOH molar ratio in the reactor feed was about 10, indicate that $CO_2$ addition significantly increases the overall acetyl yield, but unexpectedly increases the selectivity of EDDA by a factor of three, while significantly decreasing the selectivity of acetic anhydride with little effect on the selectivity of methyl acetate.

The experiments were repeated with lower values of the DME/MeOH molar ratio in the range of 2.5–4.5, and the results for experiments 16–18 of Table 11 indicate an even greater increase in the EDDA selectivity as $CO_2$ is added, while acetyl yield increased at the higher value of $CO_2$ addition.

Additional experiments were carried out at still lower values of the DME/MeOH ratio near 1.0. The results for experiments 19–20 given in Table 12 show that addition of $CO_2$ decreases the acetyl yield as well as the EDDA selectivity.

TABLE 12

Effect of CO₂ and Methanol on Hydrocarbonylation
of DME to Acetyls
(Example 7)

| Exp. No. | Feed, mmol (1.2) | | | Feed Ratios | | Acetyl Yield, % | Molar Selectivity, % | | | | | |
|---|---|---|---|---|---|---|---|---|---|---|---|---|
| | DME | MeOH | $CO_2$ | DME/MeOH | $CO_2$/MeOH | | AcH | MA | EtI | EtOAc | $Ac_2O$ | EDDA |
| 13A | 152.2 | 15.6 | 0 | 9.8 | 0 | 69.4 | 0 | 56.8 | 0 | 0.6 | 29.4 | 13.3 |
| 15$^{(3)}$ | 163.0 | 15.6 | 88.6 | 10.4 | 5.7 | 83.3 | 0 | 49.9 | 0 | 0.1 | 18.5 | 31.5 |
| 14 | 163.0 | 15.6 | 122.7 | 10.4 | 7.9 | 82.3 | 0.3 | 50.7 | 0 | 0.1 | 11.3 | 37.5 |
| 16 | 65.2 | 25.9 | 0 | 2.5 | 0 | 44.5 | 35.9 | 1.4 | 23.4 | 15.9 | Trace | 23.4 |
| 17 | 78.3 | 21.9 | 138.6 | 3.6 | 6.3 | 38.7 | 39.9 | 2.9 | 4.9 | 9.6 | 0.3 | 42.2 |
| 18 | 97.8 | 21.9 | 240.9 | 4.5 | 11.0 | 58.5 | 1.6 | 23.4 | 0.2 | 1.4 | 4.2 | 69.2 |
| 19 | 84.8 | 87.5 | 0 | 0.97 | 0 | 61.4 | 10.7 | 9.4 | 0.9 | 4.2 | 0.9 | 73.7 |
| 20 | 86.9 | 87.5 | 163.6 | 0.99 | 1.9 | 52.4 | 18.9 | 11.2 | 0.8 | 4.6 | 0.2 | 64.2 |

$^{(1)}$Syngas feed 50% CO/50% $H_2$ (molar); total pressure 1500 psig; temperature 190° C.
$^{(2)}$0.2 g $RhCl_3.3H_2O$, 135 ml acetic acid, 63.4 mmol MeI, 11.2 mmol LiI, 12.1 mmol LiOAc added with feed
$^{(3)}$Used 64.0 mol MeI Thus when acetyl reactor feed is provided directly from the LPDME reactor and EDDA is a desired product, the inclusion of $CO_2$ in the reactor feed is a preferred mode of operation. The preferred range of the DME/MeOH molar ratio for improved EDDA selectivity is about 3 to 11, although higher ratios are expected to give still higher EDDA selectivity. The preferred range of the molar ratio $CO_2$/MeOH is about 3 to 15, and more preferably 5 to 12. These preferred ranges can be realized when the feed to LP oxygenated acetyl reactor system 301 of FIG. 1 is provided directly from liquid phase dimethyl ether reactor system 201. This preferred mode of operation requires no additional treatment of effluent stream 19 of reactor system 201 as long as the water content is below about 2 mol %. Water optionally can be removed by condensation if present at higher concentrations. Feed composition, catalyst composition, and operating conditions in DME reactor system 103 can be controlled to yield the preferred composition range in feed 25 to reactor system 301. Optionally $CO_2$ 28 can be added if required.

The present invention thus allows the production of oxygenated acetyl compounds directly from synthesis gas via the liquid phase dimethyl ether process followed directly by a liquid phase acetyl reactor system. Several variations to the disclosed process are possible within the scope of the present invention. These variations impart flexibility and utility to the process, and can be used in alternative applications depending on the desired mix of products and available feedstocks. The product slate can include one or more of the oxygenated acetyl compounds vinyl acetate, acetaldehyde, ethylidene diacetate, acetic acid, methyl acetate, and acetic anhydride. The operation of the acetyl reactor system with a feed containing methanol, DME, and syngas is improved unexpectedly by the inclusion of $CO_2$ in the feed, particularly when EDDA is the preferred reactor product. Unwanted coproducts are conveniently recycled to the POX reactor which reduced the POX feed requirements.

The essential characteristics of the present invention are described completely in the foregoing disclosure. One skilled in the art can understand the invention and make various modifications thereto without departing from the basic spirit thereof, and without departing from the scope and range of equivalents of the claims which follow.

We claim:

1. A process for the synthesis of ethylidene diacetate which comprises reacting a feed containing dimethyl ether, methanol, and synthesis gas which contains hydrogen, carbon monoxide, and carbon dioxide in a liquid phase reactor containing at least acetic acid and a catalyst system consisting essentially of a Group VIII metal, methyl iodide, lithium iodide, and lithium acetate at conditions sufficient to react the components in said feed with acetic acid to produce said ethylidene diacetate and one or more additional oxygenated acetyl compounds, wherein the molar ratio of carbon dioxide to methanol in said feed is between 5 and 12.

2. The process of claim 1 wherein the molar ratio of dimethyl ether to methanol in said feed is between 3 and 11.

3. The process of claim 1 wherein the molar ratio of carbon monoxide to hydrogen in said feed is between 0.6 and 4.0.

4. The process of claim 1 wherein said one or more additional oxygenated acetyl compounds are selected from the group consisting of acetaldehyde, acetic acid, acetic anhydride, and methyl acetate.

5. The process of claim 1 wherein said synthesis gas is produced by the partial oxidation of a carbonaceous feedstock in a partial oxidation reactor system.

6. The process of claim 5 wherein said carbonaceous feedstock is selected from the group consisting of methane, natural gas, $C_2^+$ gaseous hydrocarbons, naphtha, gas oil, vacuum residuum, petroleum coke, and coal.

7. The process of claim 1 wherein said Group VIII metal is rhodium (III) chloride trihydrate.

8. The process of claim 1 wherein the liquid in said liquid phase reactor comprises one or more of said additional oxygenated acetyl compounds.

9. A process for the synthesis of ethylidene diacetate which comprises:

(a) reacting synthesis gas comprising hydrogen, carbon monoxide, and carbon dioxide in a first liquid phase reactor in the presence of a methanol synthesis catalyst and a methanol dehydration catalyst suspended in an inert liquid at conditions sufficient to produce dimethyl ether and methanol;

(b) withdrawing from said first reactor an intermediate stream comprising dimethyl ether, methanol, and unreacted synthesis gas;

(c) passing said intermediate stream into a second liquid phase reactor containing at least acetic acid and reacting said dimethyl ether, methanol, and unreacted synthesis gas which contains hydrogen, carbon monoxide, and carbon dioxide with acetic acid in the presence of a catalyst system consisting essentially of a Group VIII metal, methyl iodide, lithium iodide, and lithium acetate at conditions sufficient to produce said ethylidene diacetate and one or more additional oxygenated acetyl compounds, wherein the molar ratio of carbon dioxide to methanol in said intermediate stream is between 5 and 12; and (d) withdrawing from said second liquid phase reactor a liquid stream which contains said ethylidene diacetate and one or more additional oxygenated acetyl compounds and a vapor stream which contains unreacted synthesis gas.

10. The process of claim 9 wherein the molar ratio of dimethyl ether to methanol in said intermediate stream is between 3 and 11.

11. The process of claim 9 wherein the molar ratio of carbon monoxide to hydrogen in said intermediate stream is between 0.6 and 4.0.

12. The process of claim 9 wherein said one or more additional oxygenated acetyl compounds are selected from the group consisting of acetaldehyde, acetic acid, acetic anhydride, and methyl acetate.

13. The process of claim 9 wherein said methanol dehydration catalyst is selected from the group consisting of alumina, silica-alumina, zeolites, solid acids, solid ion exchange resins, and mixtures thereof.

14. The process of claim 9 wherein said methanol synthesis catalyst comprises copper and said methanol dehydration catalyst comprises alumina, wherein the methanol synthesis catalyst is between 75 and 90% of the methanol synthesis catalyst plus methanol dehydration catalyst on a weight basis.

15. The process of claim 9 wherein said first liquid phase reactor is operated at a temperature between 440° and 520° F., a pressure between 750 and 2,000 psig, and a gas hourly space velocity of between 3,000 and 15,000 standard liters/ (kg catalyst-hr).

16. In a process for synthesizing one or more oxygenated acetyl compounds selected from the group consisting of ethylidene diacetate, acetaldehyde, acetic acid, acetic anhydride, and methylacetate from a feed containing dimethyl ether, hydrogen, and carbon monoxide in a liquid phase reactor in the presence of a catalyst system consisting essentially of a Group VIII metal, methyl iodide, and lithium iodide, the improvement which comprises increasing the yield of said oxygenated acetyl compounds by adding carbon dioxide to said feed such that the molar ratio of carbon dioxide to dimethyl ether is between 0.3 and 1.3, wherein said liquid phase reactor contains at least acetic acid.

17. The process of claim 16 wherein the molar ratio of carbon monoxide to hydrogen in said feed is between 0.6 and 4.0.

18. The process of claim 16 wherein said Group VIII metal is rhodium (III) chloride trihydrate.

19. The process of claim 16 wherein the liquid in said liquid phase reactor comprises one or more of said oxygenated acetyl compounds.

* * * * *